United States Patent

Scafetta et al.

[11] Patent Number: 6,124,360
[45] Date of Patent: Sep. 26, 2000

[54] SOLID COMPOSITIONS SUITABLE FOR ORAL ADMINISTRATION COMPRISING NON HYGROSCOPIC SALTS OF L-CARNITINE AND ALKANOYL-L-CARNITINE WITH 2-AMINOETHANESULFONIC ACID

[75] Inventors: Nazareno Scafetta, Pavona di Albano; Maria Ornella Tinti, Rome, both of Italy

[73] Assignee: Sigma-Tau Industrie Farmaceutiche Riunite S.p.A., Rome, Italy

[21] Appl. No.: 09/381,806

[22] PCT Filed: Mar. 19, 1998

[86] PCT No.: PCT/IT98/00060

§ 371 Date: Sep. 24, 1999

§ 102(e) Date: Sep. 24, 1999

[87] PCT Pub. No.: WO98/43945

PCT Pub. Date: Oct. 8, 1998

[51] Int. Cl.⁷ .......................... A61K 31/38; A61K 31/22; C07C 67/02; C07C 229/00
[52] U.S. Cl. .......................... 514/556; 514/546; 514/561; 560/252; 560/253; 562/571
[58] Field of Search ........................ 514/546, 556, 514/561; 560/252, 253; 562/567, 571

[56] References Cited

U.S. PATENT DOCUMENTS

| 4,602,039 | 7/1986 | Cavazza . |
| 4,962,121 | 10/1990 | Hamberger et al. . |
| 5,571,783 | 11/1996 | Montagne et al. . |
| 5,589,468 | 12/1996 | Lin et al. . |

FOREIGN PATENT DOCUMENTS

| 0 207 437 | 1/1987 | European Pat. Off. . |
| 0 402 755 | 12/1990 | European Pat. Off. . |
| 0 434 088 | 6/1991 | European Pat. Off. . |
| 0 628 309 | 12/1994 | European Pat. Off. . |
| 2 529 545 | 1/1984 | France . |
| 1 153 640 | 5/1969 | United Kingdom . |

*Primary Examiner*—Gary Geist
*Assistant Examiner*—Leigh C. Maier
*Attorney, Agent, or Firm*—Nixon & Vanderhye

[57] ABSTRACT

Stable and non hygroscopic salts of L-carnitine or lower alkanoyl-L-carnitine with 2-aminoethanesulfonic acid are disclosed suitable for preparing solid compositions useful as dietary/nutritional supplements for human use and as fodder supplement for veterinary purposes.

9 Claims, No Drawings

SOLID COMPOSITIONS SUITABLE FOR ORAL ADMINISTRATION COMPRISING NON HYGROSCOPIC SALTS OF L-CARNITINE AND ALKANOYL-L-CARNITINE WITH 2-AMINOETHANESULFONIC ACID

The present invention relates to stable, non-hygroscopic, pharmacologically acceptable salts of L-carnitine and lower alkanoyl-L-carnitines which favourably lend themselves to the preparation of solid, orally administrable compositions. The present invention also relates to such compositions.

Various therapeutic uses of L-carnitine and alkanoyl derivatives thereof are already known. For instance, L-carnitine is used in the cardiovascular field for the treatment of acute and chronic myocardial ischaemia, angina pectoris, heart failure and cardiac arrhythmias.

In the nephrological field, L-carnitine is administered to chronic uraemics undergoing regular haemodialytic treatment to combat myasthenia and the onset of muscular cramps.

Other therapeutic uses relate to the normalization of the HDL:LDL+VLDL ratio and total parenteral nutrition.

It is also known that the salts of L(−)-carnitine and its alkanoyl derivatives present the same therapeutic or nutritional activities as those of the so-called inner salts and can, therefore, be used in their place, provided these salts are "pharmacologically acceptable", i.e. they do not present unwanted toxic or side effects.

In practice, then, the choice between an "inner salt" and a true L(−)-carnitine or alkanoyl-L(−)-carnitine salt will depend essentially on availability, economical and pharmacy considerations rather than on therapeutic or nutritional considerations.

The object of the present invention is to provide stable and non-hygroscopic salts of L-carnitine and lower alkanoyl-L-carnitines which are endowed with an enhanced therapeutical and/or nutritional efficacy with respect to their inner salt counterparts.

It should, therefore, be clearly understood that the utility of the salts of the present invention is not confined to their lack of hygroscopicity and higher stability compared to the corresponding inner salts, but also resides in the contribution to the overall therapeutic and/or nutritional value of the salt in its entirety provided by their anionic moiety. This value is, therefore, no longer to be attributed exclusively to the "carnitine" moiety of the salt.

Because of their lack of hygroscopicity these salts can be easily compounded, particularly with a view of preparing solid, orally administrable compositions.

As is well known to experts in pharmacy, the processing of hygroscopic products entails the use of controlled-humidity chambers both for storage and for the processing itself.

Moreover, the finished products must be packed in hermetically sealed blisters in order to avoid unpleasant consequences due to humidity.

All this involves extra costs both for the storage of raw materials and for their processing and packaging.

Among the populations of the industrialised countries there is an increasingly widespread use of food supplements or "nutraceuticals" both by sportsmen (amateurs or professionals) and by people in good health.

The former use L-carnitine or food supplements containing L-carnitine because it facilitates the oxidation of fatty acids and makes a larger amount of energy available to skeletal muscle, thus allowing enhanced performance and giving rise to less accumulation of lactic acid in the athletes' muscles.

People in good health use these food supplements as health foods, i.e. for the purposes of favouring a reduction in serum fat levels and normalisation of the ratio between the various cholesterol fractions in order to prevent diseases related to lipid metabolism disorders.

It has been estimated that the amount of L-carnitine and its derivatives sold for non-ethical purposes is twice that sold for ethical purposes.

The US market for food supplements or nutraceuticals amount to approximately 250 billion dollars, whereas the estimated figure for the European market is approximately 500 billion dollars (Food Labeling News, 1994, "Nutraceuticals" Market said to be a vast one, March, Vol. 2, n° 25; King Communications Group Inc., 1993, "Nutraceuticals" Foods, Drink in Global Market Food and Drink Daily, April, Vol. 3, n° 503).

Some non-hygroscopic salts of L-carnitine are already known.

For instance EP 0 434 088 (LONZA) filed Dec. 21, 1990 discloses the use of the non-hygroscopic L(−)carnitine L(+) tartrare (2:1) (the preparation and physico-chemical characterization of which were, however, described by D. Müller and E. Strack in Hoppe Seyler's Z. Physiol. Chem 353, 618–622. April 1972) for the preparation of solid forms suitable for oral administration.

This salt presents, however, some drawbacks, such as e.g. the release, after prolonged storage, of traces of trimethylamine which give the product an unpleasant fishy odour. Moreover, L(−)-carnitine L(+)-tartrate (2:1) becomes deliquescent at relative humidity slightly exceeding 60%. Furthermore, L-(+)-tartaric acid is unable to give non-hygroscopic salts with the alkanoyl-L-carnitines, such as e.g. acetyl-L-carnitine.

The aforesaid object of the present invention, i.e. to provide novel, stable and non-hygroscopic pharmacologically acceptable salts of both L-carnitine and lower alkanoyl-L-carnitines wherein the anion moiety contributes to the therapeutic and/or nutritional value of the salt, is achieved by the salts of formula (I) wherein the salt anion is the anion of 2-aminoethanesulfonic acid (or taurine):

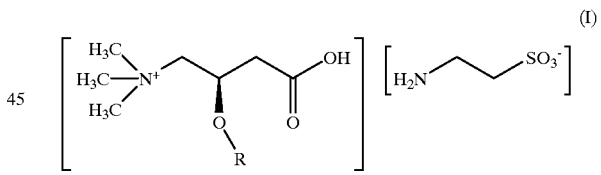

wherein R is hydrogen or straight or branched lower alkanoyl, having 2–5 carbon atoms.

The preferred salts are those wherein R is selected from the group comprising acetyl, propionyl, butyryl, valeryl and isovaleryl.

Taurine or 2-aminoethanesulphonic acid is one of the most plentiful amino acids in the body and is to be found in the central nervous system and skeletal muscles as well as being concentrated in the brain and heart.

It has long been known to be an essential nutrient during mammalian growth and development, and is, in fact, present in mother's milk and is especially important for the development of the cerebellum and retina.

Taurine also performs a very important metabolic function: in the bile, the bile acids bind with taurine to form glycocholic and taurocholic acid, respectively.

The salts of bile acids possess the important property of lowering the surface tension of solutions. For this reason they are excellent emulsifiers and perform an important function in the uptake and digestion of lipids in the bowel.

These important metabolic and nutritional characteristics enable taurine, when bound to L-carnitine, to perform a complementary task to that performed by the latter.

In fact, taurine, by favouring the emulsification and digestion of fatty acids, exerts an activity which is complementary to the subsequent metabolic activity exerted by L-carnitine, i.e. the oxidation of fatty acids for the production of energy.

This complementarity of the metabolic action of the two salt moieties (i.e. L-carnitine and taurine) is particularly useful in human or animal nutrition both in physiological conditions, i.e. in state of good health, and in the malabsorption syndrome occurring in children and adults.

The new salts prove particularly useful as food supplements for sportsmen (amateur or professionals) also by virtue of the additional energy output facilitated by taurine. In people in good health they act as health food because they promote the digestion of fats and prevent diseases related to lipid metabolism disorders.

The salts of formula (I) are non-hygroscopic and highly stable to prolonged storage.

The following non-limiting examples show the preparation of some non-hygroscopic salts according to the present invention.

EXAMPLE 1

Preparation of L-carnitine 2-aminoethanesulfonate (ST 1290)

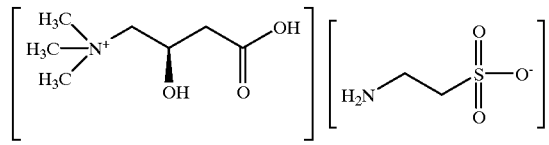

L-carnitine inner salt (3.2 g; 0.02 moles) and taurine (2.5 g; 0.02 moles) were dissolved in water (final volume 100 mL). The resulting solution was concentrated under vacuum.

The residue was taken up with isobutanol and the resulting mixture concentrated under vacuum to remove water. The raw reaction product was suspended in acetone the resulting mixture kept under stirring at room temperature overnight and then filtered.

5.6 g of a solid, non-hygroscopic solid were obtained.
M.P.=170° C. (dec.)
$[\alpha]_D^{25}=-15.9$ (c=1%, $H_2O$)
HPLC:

| Stationary phase | SGE-SAX (5 μm) 250 × 4.0 mm, t = 25° C. | |
|---|---|---|
| Eluant | $CH_3CN/KH_2PO_4$ 50 mM 72/28 pH 5.6 | |
| Flow-rate | 0.75 mL/min | |
| $R_t$ L-carnitine | 11.9 min | 51.3% |
| $R_t$ taurine | 9.7 min | 44.3% |
| $H_2O$ (K. F. method) | | 5.7% |

| Elementary analysis for $C_9H_{21}N_2O_6S$ | | | |
|---|---|---|---|
| | C % | H % | N % |
| Calculated (with 5.7% $H_2O$) | 35.72 | 7.63 | 9.25 |
| Found | 35.32 | 8.31 | 9.10 |

NMR $D_2O$ δ 4.4(m,1H,C$\underline{H}$OH); 3.3(4H,m,$N^+CH_2$;$NH_2C\underline{H}_2$); 3.1-3.0(13H,d+s,$(CH_3)_3N^+$;$CH_2SO_3$); 2.2(2H,d,$CH_2COO$)

EXAMPLE 2

Preparation of acetyl L-carnitine 2-aminoethanesulfonate (ST 1294)

Acetyl L-carnitine 2-aminoethanesulfonate was prepared as described in Example 1.

A solid, non-hygroscopic compound was obtained.
M.P.=140° C. (dec.)
$[\alpha]_D^{25}=-15.06$ (c=1%, $H_2O$)
HPLC:

| Stationary phase | Spherisorb SCX (5 μm) 250 × 4 mm, t = 25° C. | |
|---|---|---|
| Eluant | $CH_3CN/NH_4H_2PO_4$ 50 mM 60/40 pH 4 | |
| Flow-rate | 0.75 mL/min | |
| $R_t$ acetyl L-carnitine | 12.08 min | 54% |
| $R_t$ taurine | 4.711 min | 41% |
| $H_2O$ | | 6.4% |

| Elementary analysis for $C_{11}H_{24}N_2O_7S$ | | | |
|---|---|---|---|
| | C % | H % | N % |
| Calculated (with 6.4% $H_2O$) | 37.65 | 7.61 | 7.98 |
| Found | 36.86 | 7.45 | 7.92 |

NMR $D_2O$ δ 5.6(1H,m,CHOCO); 3.9-3.4(2H,m,$N^+CH_2$); 3.4(2H,t,$NH_2C\underline{H}_2$); 3.3-3.1(2H,t,$CH_2SO_3$; 9H,s,$(CH_3)_3N^+$); 2.4-2.5(2H,m,$CH_2COO$); 2.1 (3H,s,$COCH_3$)

The compounds of the foregoing examples are non-hygroscopic and highly stable.

The present invention also relates to compositions comprising as active principle(s) at least one of the aforesaid non-hygroscopic pharmacologically acceptable salts and, optionally, one or more pharmacologically acceptable excipients and active ingredients which are well-known to the experts in pharmacy and food technology.

Particularly preferred are the solid, orally administrable compositions such as tablets chewable tablets and capsules, which comprise a salt of L-carnitine or alkanoyl-L-carnitine of formula (I) in an amount corresponding to 50–2,000, preferably 100–1,000, mg of L-carnitine or alkanoyl-L-carnitine inner salt.

For instance, a composition for preparing tablets is the following:

| Non-hygroscopic L-carnitine salt of formula (I) | 500 mg |
|---|---|
| Starch | 20 mg |
| Talc | 10 mg |
| Calcium stearate | 1 mg |
| | 531 mg |

A composition suitable for preparing capsules is the following:

| Non-hygroscopic L-carnitine salt of formula (I) | 500 mg |
|---|---|
| Starch | 20 mg |
| Lactose | 50 mg |
| Talc | 5 mg |
| Calcium stearate | 2 mg |
| | 577 mg |

The compositions of the present invention may be used as dietary/nutritional supplements for human use or as fodder supplement for veterinary purposes.

What is claimed is:

1. A salt of L-carnitine or alkanoyl-L-carnitine with 2-aminoethanesulfonic acid, of formula (I)

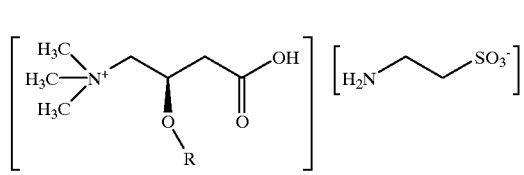

wherein R is hydrogen or straight or branched lower alkanoyl having 2–5 carbon atoms.

2. The salt of claim 1, wherein R is selected from the group comprising acetyl, propionyl, butyryl, valeryl and isovaleryl.

3. A composition comprising as active ingredient a salt of general formula (I) as defined in claim 1.

4. The composition of claim 3, further comprising one or more substances selected from pharmacologically acceptable excipients and active ingredients.

5. The composition of claim 3, in the form of tablets, chewable tablets, capsules, granulates or powders.

6. The composition of claim 3, in unit dosage form comprising as active ingredient a salt of L-carnitine or alkanoyl-L-carnitine of formula (I), in an amount corresponding to 50–2,000, of L-carnitine or alkanoyl-L-carnitine inner salt.

7. The composition of claims 3 as dietary/nutritional supplement for human use.

8. The composition of claims 3 as fodder supplement for veterinary use.

9. The composition of claim 3 in unit dosage form comprising as active ingredient a salt of L-carnitine of formula (I), in an amount corresponding to 100–1000 mg of L-carnitine or alkanoyl-L-carnitine inner salt.

* * * * *

UNITED STATES PATENT AND TRADEMARK OFFICE

CERTIFICATE OF CORRECTION

PATENT NO. : 6,124,360
DATED : September 26, 2000
INVENTOR(S) : SCAFETTA et al

It is certified that error appears in the above-identified patent and that said letters patent is hereby corrected as shown below:

Please add the following information on the cover page of the patent

[50] Foreign Application Priority Data

April 1, 1997   [IT]   Italy...............RM97A000184

Signed and Sealed this

Eighth Day of May, 2001

Attest:

NICHOLAS P. GODICI

Attesting Officer    Acting Director of the United States Patent and Trademark Office